United States Patent
Han et al.

(10) Patent No.: US 10,106,402 B2
(45) Date of Patent: Oct. 23, 2018

(54) BIOMEDICAL IMPLANTS COMPRISING SURFACE-MODIFIED METAL PARTICLES AND BIODEGRADABLE POLYMERS, ITS USE FOR SUPPRESSING INFLAMMATION, AND PREPARATION METHOD THEREOF

(75) Inventors: Dong Keun Han, Seoul (KR); Kwi Deok Park, Seoul (KR); Jong Hee Kang, Seoul (KR); Bong Soo Lee, Daejeon (KR); Ji Yeon Choi, Seoul (KR); Chang Hun Kum, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 12/985,549

(22) Filed: Jan. 6, 2011

(65) Prior Publication Data
US 2012/0070650 A1  Mar. 22, 2012

(30) Foreign Application Priority Data
Sep. 16, 2010  (KR) .................. 10-2010-0091028

(51) Int. Cl.
| | | |
|---|---|---|
| *B32B 5/16* | (2006.01) | |
| *A61L 31/10* | (2006.01) | |
| *B82Y 5/00* | (2011.01) | |
| *A61L 17/06* | (2006.01) | |
| *A61L 27/04* | (2006.01) | |
| *A61L 27/34* | (2006.01) | |
| *A61L 27/58* | (2006.01) | |
| *A61L 31/02* | (2006.01) | |
| *A61L 31/14* | (2006.01) | |

(52) U.S. Cl.
CPC ............... *B82Y 5/00* (2013.01); *A61L 17/06* (2013.01); *A61L 27/04* (2013.01); *A61L 27/34* (2013.01); *A61L 27/58* (2013.01); *A61L 31/02* (2013.01); *A61L 31/10* (2013.01); *A61L 31/148* (2013.01); *Y10T 428/254* (2015.01)

(58) Field of Classification Search
USPC ....................................................... 428/327
See application file for complete search history.

(56) References Cited

U.S. PATENT DOCUMENTS

| | | | | |
|---|---|---|---|---|
| 2002/0115742 | A1* | 8/2002 | Trieu et al. .................... | 523/113 |
| 2004/0078077 | A1* | 4/2004 | Binette et al. ............. | 623/13.17 |
| 2008/0008654 | A1* | 1/2008 | Clarke et al. .................. | 424/9.4 |
| 2008/0119927 | A1* | 5/2008 | Lessar .......................... | 623/1.42 |
| 2009/0297581 | A1 | 1/2009 | Young | |
| 2009/0309597 | A1* | 12/2009 | Horak et al. ................... | 324/318 |
| 2010/0008854 | A1* | 1/2010 | Haam et al. ................. | 424/1.61 |

FOREIGN PATENT DOCUMENTS

| | | |
|---|---|---|
| KR | 10-2007-0102717 | 10/2007 |
| KR | 10-2009-0082814 | 7/2009 |

OTHER PUBLICATIONS

Office Action dated Jul. 18, 2012, issued by the Korean Intellectual Property Office in prosecuting the corresponding Korean Patent Application No. 10-2010-0091028.
English translation of Abstract of KR10-2007-0102717.
English translation of Abstract of KR10-2009-0082814.
Office Action dated Feb. 26, 2013 in Korean Patent Application No. 10-2010-0091028, 14 pages.
Lee et al., "The effect of surface-modified nano-hydroxyapatite on bilcompatibility of poly(•-caprolactone)/hydroxyapatite nanocomposites," European Polymer Journal 2007, vol. 43, Feb. 28, 2007, pp. 1602-1608.
Schiller et al., "Carbonated calcium phosphate are suitable pH-stabilising fillers for biodegradable polyesters," Biomaterials 2003, vol. 24, Dec. 17, 2002, pp. 2037-2043.
Van Der Meer et al. "The influence of basic filler materials on the degradation of amorphous D- and L-lactide copolymer" Journal of Materials Science: Materials in Medicine, 7 (1996) 359-361.

* cited by examiner

*Primary Examiner* — Cheng Yuan Huang
(74) *Attorney, Agent, or Firm* — Vierra Magen Marcus LLP

(57) ABSTRACT

Disclosed are biomedical implants comprising surface-modified metal particles and biodegradable polymers; its use for suppressing inflammation; and a method for preparing a biomedical material, comprising: (a) modifying surface of basic metal particles with a polymer to obtain surface-modified metal particles; and (b) mixing the surface-modified metal particles with a biodegradable polymer, followed by manufacturing a biodegradable biomedical implant, or coating the resulting mixture on a conventional biomedical implant.

5 Claims, No Drawings

BIOMEDICAL IMPLANTS COMPRISING SURFACE-MODIFIED METAL PARTICLES AND BIODEGRADABLE POLYMERS, ITS USE FOR SUPPRESSING INFLAMMATION, AND PREPARATION METHOD THEREOF

This application claims priority from Korean Patent Application No. 10-2010-0091028, filed on Sep. 16, 2010, which is herein expressly incorporated by reference in its entirety.

FIELD OF THE INVENTION

The present invention relates to biomedical implants comprising surface-modified metal particles and biodegradable polymers, its use for suppressing inflammation, and a preparation method thereof.

DESCRIPTION OF THE RELATED ART

Recently, according to the development of the medical technology, artificial organs or implantation materials have been used to substitute or recover damaged organs within a human body, and such materials are called as biomedical implants. Applications of the biomedical implants have been gradually extending, and thus, researches have been widely conducted for the development of biomedical implants. Materials used for the biomedical implants include polymers, metals, ceramics, composite materials, and the like. However, the material to be used in vivo must have biocompoatibility, and it needs to have blood compatibility when it is in contact with blood, and it needs to have tissue compatibility when it is in contact with a biological tissue, which result in limitation on available biomedical materials.

Thus, polymer materials having excellent formability and stable physical properties while being harmless to a human body were highlighted. In particular, biodegradable polymers have the characteristics in which they are degraded after the lapse of a certain period of time, which makes it possible to minimize a foreign body reaction due to an immunological reaction when the biomedical implants are applied in vivo.

However, biodegradable polymers have relatively poor physical properties compared with other polymers, and when they are biodegraded, acidic material such as lactic acid, glycolic acid, hydroxy caproic acid, maleic acid, phosphagen, hydroxy butyrate, hydroxyethoxy acetic acid, sebacic acid, alcohols, trimethyleneglycol, amino acids, formalin, alkylcyanoacrylate, and the like, are generated, which cause inflammation reactions and cytotoxicity within a human body.

Albeit the shortcomings as mentioned above, biodegradable polymers have been widely used for biomedical implants owing to the characteristics that they are completely degraded after the lapse of a certain period of time. Some methods for alleviating inflammation reactions of biodegradable polymers have also been suggested.

For example, researches for obtaining an inflammation suppressing effect and improving physical properties by containing a nonsteroidal antiinflammatory drug, such as an ester of salicylic acid, acetylsalicylic acid, or the like, have been conducted (J. Mater. Sci. Mater. Med., 13, 1051-1055, 2002), and a method for suppressing both inflammation and restenosis by coating pyridoxal-5-phosphate on a stent has been suggested (WO 2006/056038). Also, a method for suppressing cell inflammation by making COX-2 protein and iNOS protein expressed with a taheebo extract has been suggested (KR 10-2008-0092263A). In addition, a method of inducing the suppression of nitric oxide generation, which is occurred during an inflammatory reaction, with gold and silver nanoparticles has been studied (KR 10-2009-0080855A).

However, the methods as mentioned above are to suppress already induced inflammations by containing an anti-inflammatory drug in biomaterials, which may result in side effects due to the use of drugs.

Furthermore, a method for completely suppressing generation of acidic byproducts resulting from the degradation of biodegradable polymers has not yet been suggested. Namely, cell inflammation reactions due to the acidic byproducts have been constantly induced by the biodegradation of biodegradable polymers, but no fundamental solution thereto has been suggested, and there is a limitation on the improvement of physical and mechanical properties of biodegradable polymers.

SUMMARY OF THE INVENTION

An object of the present invention is to provide a method for suppressing inflammation reactions or cytotoxicity caused by acidic byproducts of low pHs, which are generated by the degradation of biodegradable polymers in biomedical implants, by neutralizing the acidic byproducts with a basic metal which is harmless to a human body and is degradable.

Another object of the present invention is to provide a method for improving physical and mechanical properties of biodegradable polymer materials, by modifying the surface of basic metal particles, so as to control basic characteristics and to improve compatibility of the basic metal particles with biodegradable polymers.

In order to achieve the above objects, there are provided of the following:

(1) A biomedical implant comprising: basic metal particles of which surface are modified with a polymer; and a biodegradable polymer;

(2) A method for preparing a biomedical material according to (1) above, comprising: (a) modifying surface of basic metal particles with a polymer to obtain surface-modified metal particles; and (b) mixing the surface-modified metal particles obtained in step (a) with a biodegradable polymer, followed by manufacturing a biodegradable biomedical implant; and (3) A method for preparing a biomedical implant, comprising: (a) modifying a surface of basic metal particles with polymer to obtain surface-modified metal particles; and (c) mixing the surface-modified metal particles obtained in step (a) with biodegradable polymers and coating the resulting mixture on the surface of a biomedical implant.

According to the present invention, biomedical implants comprising surface-modified metal particles and biodegradable polymers, its use for suppressing inflammation, and a preparation method thereof are provided.

Biodegradable polymers are mixed with surface-modified basic metal particles, thereby improving physical and mechanical properties of the biodegradable polymer materials can be improved, and acidic byproducts generated from the degradation of biodegradable polymers can be neutralized by a basic metal, by which inflammation reactions and cytotoxicity caused by the acidic byproducts can be remarkably improved.

Therefore, biomedical implants can be directly prepared using the basic metal particles of which surface are modified by polymers and biodegradable polymers, or the basic metal particles of which surface are modified by polymers and biodegradable polymers can be usefully coated on conventional biomedical implants made of polymer, metal, ceramic, or composite material, such as cardiovascular system materials such as stent, suture for a surgical operation, support for tissue regeneration, bio-nanofiber, hydrogel, biosponge, and the like; dental material such as pin, screw, bar, and the like; material for neurological, orthopaedic or plastic surgery; and the like.

DETAILED DESCRIPTION OF THE INVENTION

The present invention relates to biomedical implants comprising surface-modified basic metal particles and biodegradable polymers, its use for suppressing inflammation, and a preparation method thereof.

The basic metal particles may be at least one selected from the group consisting of particles of a metal selected from the group consisting of alkali metals and alkaline earth metals, and particles of a metal compound selected from the group consisting of hydroxides of alkali metals, oxides of alkali metals, hydroxides of alkaline earth metals, and oxides of alkaline earth metals. The alkali metal or alkaline earth metal may be lithium, beryllium, sodium, magnesium, potassium, calcium, rubidium, strontium, barium, cesium, francium and radium, and the metal compound may be at least one selected from the group consisting of lithium hydroxide, beryllium hydroxide, sodium hydroxide, magnesium hydroxide, potassium hydroxide, calcium hydroxide, rubidium hydroxide, strontium hydroxide, barium hydroxide, cesium hydroxide, francium hydroxide, radium hydroxide, lithium oxide, sodium oxide, magnesium oxide, manganese oxide, potassium oxide, calcium oxide, barium oxide, cesium oxide and radium oxide.

Surface area of the metal particles may change depending on their diameters, which results in change of the degree and speed of neutralization of the metal particles. In addition, in order to modify the surface of the metal particles, the particle size may be at least 1 nm. If the size of the metal particle exceeds 1 mm, a polymer matrix is undesirably cracked to deteriorate physical properties. Thus, a preferable diameter of the metal particles ranges from 1 nm to 1 mm.

The polymer used for modifying the surface of the metal particles may be polymers generated by the polymerization of one or more monomers selected from the group consisting of lactide, glycolide, caprolactone, dioxanone, trimethylenecarbonate, hydroxyalkanoate, peptides, cyanoacrylate, lactic acid, glycolic acid, hydroxycaproic acid, maleic acid, phosphazene, amino acid, hydroxybutyric acid, sebacic acid, hydroxyethoxy acetic acid, and trimethyleneglycol.

The polymer used for modifying the surface of the basic metal particles may be at least one selected from the group consisting of polylactide, polyglycolide, polycaprolactone, poly(lactide-co-glycolide), poly(lactide-co-caprolactone), poly(glycolide-co-caprolactone), polydioxanone, polytrimethylene-carbonate, poly(glycolide-co-dioxanone), polyamideester, polypeptide, polyortho-esters, polymaleic acid, polyphosphazene, polyanhydride, polycebacicanhydride, polyhydroxyalkanoate, polyhydroxy butylate, and polycyanoacrylate.

Preferably, the content of the polymer is 5 to 95 wt % and the content of basic metal particles is 5 to 95 wt % with respect to the total weight of the surface-modified basic metal particles. In the surface-modified basic metal particles, the ratio of the surface-modified layer of the metal particles depends on the weight ratio between the basic metal particles and the polymer, and thus, the speed and the degree of neutralization of the metal particles can be controlled. If the content of the basic metal particles is less than 5 wt %, the amount of the polymer on the surface of the metal particles is so large as to make the neutralization function of the basic metal particles impossible. If the content of the metal particles exceeds 95 wt %, the surface modification of the metal particles is not sufficient.

The biodegradable polymer may be one or more selected from the group consisting of polylactide, polyglycolide, polycaprolactone, poly(lactide-co-glycolide), poly(lactide-co-caprolactone), poly(glycolide-co-caprolactone), polydioxanone, polytrimethylenecarbonate, poly(glycolide-co-dioxanone), polyamideester, polypeptide, polyorthoester group, polymaleic acid, polyphosphazene, polyanhydride, polycebacicanhydride, polyhydroxyalkanoate, polyhydroxybutylate, and polycyanoacrylate.

The biomedical implant according to the present invention may be made of the basic metal particles of which surface are modified with a polymer and a biodegradable polymer, or may be one in which the basic metal particles of which surface are modified with a polymer and a biodegradable polymer are coated on a conventional biomedical implant.

When the biomedical implant according to the present invention is made of the basic metal particles of which surface are modified with a polymer and a biodegradable polymer, the content of the basic metal particles of which surface are modified with polymer is adjusted in the range of 1 wt % to 99 wt % and the content of the biodegradable polymer is adjusted in the range of 1 wt % to 99 wt % with respect to the total weight of the biomedical implant. In the present invention, the content of the metal particles and the biodegradable polymer may be adjusted in the ranges above, by which the physical properties and the degree of neutralization of the biomedical implant can be controlled.

The biomedical implant may be a cardiovascular system material such as stent, suture for a surgical operation, support for tissue regeneration, bio-nanofiber, hydrogel, bio-sponge, and the like; dental material such as pin, screw, bar, and the like; or material for neurological, orthopaedic and plastic surgeries; and the like, but not limited thereto, and the biomedical implant may be any other biomedical implants.

When the biomedical implant according to the present invention is the one in which the basic metal particles of which surface are modified with a polymer and a biodegradable polymer are coated on a conventional biomedical implant, the coating contains the basic metal particles of which surface are modified with a polymer in an amount of 1 wt % to 99 wt % and the biodegradable polymer in an amount of 1 wt % to 99 wt % with respect to the total weight of the coating. The characteristics of the degree of neutralization can be controlled by adjusting the content of the basic metal particles in the layer of the coating. In the present invention, the content ratio of the basic metal particles and the biodegradable polymers in the coated layer is adjusted, thereby making it possible to apply to a wide range of biomedical implants.

The conventional biomedical implant may be any biomedical implant made of a material of metal, ceramic, composite material, non-degradable polymer or biodegradable polymer material. In particular, the material may be selected from the group consisting of metal selected from iron, copper, gold, silver, platinum, stainless steel, cobalt-chromium, platinum-chromium, cobalt alloy, titanium, titanium alloy, tantalum, nickel-titanium, nickel, nickel alloy, magnesium, and magnesium alloy; ceramic selected from the group consisting of hydroxyapatite, tetracalcium phosphate (TeCP), dicalcium phosphate (DCP), NaH2PO4, α-tricalcium phosphate (α-TCP), glycerophosphate, porous hydroxyapatite (PHA), brushite, β-tricalcium phosphate (β-TCP), monocalcium phosphate monohydrate (MCPM), MgHPO4, Na4P2O7, and CaSO4; non-degradable polymers selected from the group consisting of polyethylene, polypropylene, polyvinylalcohol, polyvinylchloride, polystyrene, polycarbonate, polyetheretherketone (PEEK), polyamide, polyacetal, polythiophene, polyethyleneoxide, polytetrafluoroethylene, an acrylic resin such as polymethylmethacrylate (PMMA), polyurethane, an epoxy resin, and polysiloxane; and biodegradable polymers selected from the group consisting of polylactide, polyglycolide, polycaprolactone, poly(lactide-co-glycolide), poly(lactide-co-caprolactone), poly(glycolide-co-caprolactone), polydioxanone, polytrimethylene-carbonate, poly(glycolide-co-dioxanone), polyamideester, polypeptide, poly-orthoesters, polymaleic acid, polyphosphazene, polyanhydride, polycebacic-anhydride, polyhydroxyalkanoate, polyhydroxybutylate, and polycyanoacrylate.

The present invention also relates to a method for preparing a biodegradable biomedical implant comprising basic metal particles of which surface are modified with a polymer and a biodegradable polymer, comprising: (a) modifying surface of basic metal particles with a polymer to obtain surface-modified metal particles; and (b) mixing the surface-modified metal particles with a biodegradable polymer to obtain the biodegradable biomedical implant.

In step (a), the surface-modified metal particles are obtained by conducting a ring-opening polymerization or condensation polymerization of at least one monomer on the surface of basic metal particles, or by encapsulating core of basic metal particles into a polymer shell in a core-shell structure.

In case of modifying the surface by ring-opening polymerization, 5 wt % to 95 wt % of basic metal particles based on total weight of the surface-modified metal particles to be obtained in step (a) is used. If the amount of the basic metal particles is less than 5 wt %, the content of the polymer on the surface of the metal particles is too high to retain the neutralization function of the metal particles, and if the amount of the metal particles exceeds 95 wt %, the surface of the metal particles are not sufficiently modified, which is thus undesirable.

The ring-opening polymerization is conducted under a condition of a vacuum heating using a typical ring-opening catalyst in an amount of 0.001 wt % to 5.0 wt % with respect to the total weight of the surface-modified metal particles to be obtained in step (a), and the ring opening catalyst may be selected from the group consisting of tin powder, stannous octoate, dibutyl tin dilaurate, dibutyltin dibromide, dibutyltin dichloride, tin(II) chloride, tin(IV) chloride, tin oxide, zinc powder, diethyl zinc, zinc octoate, zinc chloride, and dodecylbenzenesulfonic acid.

In case of modifying the surface by using the condensation polymerization, 5 wt % to 95 wt % of basic metal particles based on the total weight of the surface-modified metal particles to be obtained in step (a) is used. If the amount of the basic metal particles is less than 5 wt %, the content of the polymers on the surface of the metal particles is too high to retain the neutralization function of the metal particles, and if the amount of the metal particles exceeds 95 wt %, the surface of the metal particles are not sufficiently modified, which is thus undesirable.

The condensation polymerization is conducted under a condition of a vacuum heating. An optimum polymerization temperature for the monomers to be subjected to condensation polymerization ranges from 50° C. to 300° C., and a reaction time is 1 to 60 hours.

In case of modifying the surface of the metal particles by encapsulating in a core-shell structure, a polymer for modifying surface of basic metal particles is dissolved in a solvent, to which the basic metal particles are dispersed at 10 rpm to 100,000 rpm with an ultrasonic wave or a homogenizer, and the resulting particles are recovered, to obtain the surface-modified metal particles. The solvent may be one or more selected from the group consisting of chloroform, acetone, tetrahydrofuran, dioxane, acetonitrile, methylene chloride, toluene, xylene, benzene, and hexafluoroisopropane.

The monomers and polymers used for modifying the surface of the metal particles in step (a) are the same as described above.

In step (b), 1 to 99 weight parts of the surface-modified metal particles obtained in step (a) is mixed with 1 to 99 weight parts of a biodegradable polymer, to obtain the biodegradable biomedical implant. As the content of the surface-modified metal particles in the matrix of the biodegradable polymer increases, the degree and speed of neutralization the biomedical implant increase. Thus, the degree and speed of neutralization of the biomedical implant can be controlled by adjusting the content of the surface-modified metal particles.

Another method for preparing a biomedical implant according to the present invention, comprising basic metal particles of which surface are modified with a polymer and biodegradable polymers, may comprise, instead of step (b), (c) mixing the surface-modified metal particles obtained in step (a) with a biodegradable polymer, followed by coating the resulting mixture on the surface of a biomedical implant, to obtain a conventional biomedical implant which is coated with the mixture of the basic metal particles of which surface are modified with a polymer and biodegradable polymers.

In step (c), 1 to 99 weight parts of the surface-modified metal particles obtained in step (a) and 1 to 99 weight parts of the biodegradable polymers are mixed, and the resulting mixture is then coated on the surface of a conventional biomedical implant made of a material of metal, ceramic, composite material, non-degradable polymer, or biodegradable polymer. The characteristics of the degree of neutralization of the biomedical implant can be controlled by adjusting the content of the surface-modified metal particles in the coated layer.

As the coating method, any known coating method, such as ultrasonic method, spray method, dipping method, spin coating method, electrolytic coating method, and chemical/physical vapor deposition method, may be used.

The types of the biodegradable polymers, and the types and materials of the biomedical implants used in the steps (b) and (c) are those as described above.

EXAMPLE

Hereinafter, the present invention will now be described in detail through examples. However, the examples described hereinafter are merely illustrative and the scope of the present invention is not limited thereto.

In order to evaluate the characteristics of the biomedical implants prepared according to examples of the present invention and comparative examples, mechanical tensile strengths were determined with Instron in accordance with the method of ASTM D638, and pH changes were observed after 8 weeks from biodegradation. In addition, cell inflammations and cytotoxicity were observed with the expression of COX-2, which is an inflammation marker, and with the cytotoxicity experiments.

Example 1

50 weight parts of magnesium hydroxide and 50 weight parts of lactide were put into a dried glass reactor. 0.1 wt % of stannous octoate, as a catalyst, with respect to the total weight of the reactants (magnesium hydroxide and lactide) was diluted in toluene, and the resultant was then added to the glass reactor. The glass reactor was maintained under a vacuum at 70° C. for six hours with stirring, so as to completely remove toluene and moisture. The temperature of the sealed glass reactor was adjusted to 140° C., and the reactants were subjected to a ring-opening polymerization for 30 minutes with stifling in an oil bath. After the polymerization was completed, the polymer was recovered, put in chloroform, stirred for more than 1 hour, and filtered out to remove homo polymers and non-reacted materials, to finally obtain magnesium hydroxide particles of which surface were modified with polylactide.

Thereafter, 30 weight parts of the surface-modified magnesium hydroxide particles prepared in the foregoing manner were mixed with 70 weight parts of polylactide biodegradable polymer, and a completely biodegradable stent with the resulting mixture was manufactured. Tensile strength, pH change, inflammation reaction, and cytotoxicity were observed. As noted in Table 1, the tensile strength was remarkably improved, pH became neutral, the inflammation reaction was completely suppressed, and cytotoxicity did not appear.

Example 2

60 weight parts of calcium hydroxide and 40 weight parts of lactic acid were put into a glass reactor, and maintained under a vacuum at 70° C. for six hours with stifling, so as to completely remove moisture. The temperature of the glass reactor was adjusted to 140° C. and the reactants were subjected to a condensation-polymerization for 30 minutes in an oil bath. Non-reacted materials were removed from the recovered polymer in the same manner as described in Example 1, to obtain calcium hydroxide particles of which surface were modified with polylactide.

Thereafter, 20 weight parts of the surface-modified calcium hydroxide particles prepared in the foregoing manner were mixed with 80 weight parts of polyglycolide as a biodegradable polymer, and a suture for a surgical operation was manufactured with the resulting mixture. Tensile strength, pH change, inflammation reaction, and cytotoxicity were then measured. As noted in Table 1, the results were similar to those of Example 1.

Example 3

10 weight parts of polycaprolactone were dissolved in 85 weight parts of chloroform, to which 5 weight parts of magnesium oxide were added. The resultant was treated with ultrasonic wave for 60 minutes so as to make it completely dispersed, to obtain magnesium oxide particles of which surface were modified with polycaprolactone according to a core-shell method.

15 weight parts of the surface-modified magnesium oxide particles prepared in the foregoing manner were mixed with 85 weight parts of poly(lactide-co-glycolide), and a support for tissue regeneration was manufactured. Tensile strength, pH change, inflammation reaction, and cytotoxicity were then measured. As noted in Table 1, the results were similar to those of Example 1.

Example 4

10 weight parts of barium hydroxide and 90 weight parts of glycolide were subjected to a ring-opening polymerization in the same manner as described in Example 1, to obtain barium hydroxide particles of which surface were modified with polyglycolide.

30 weight parts of the surface-modified barium hydroxide particles prepared in the foregoing manner were mixed with 70 weight parts of polydioxanone, and a nano fiber was manufactured. Tensile strength, pH change, inflammation reaction, and cytotoxicity were then observed. As noted in Table 1, the results were similar to those of Example 1.

Example 5

20 weight parts of potassium oxide and 80 weight parts of caprolactone were subjected to a ring-opening polymerization in the same manner as described in Example 1, to obtain potassium oxide particles of which surface were modified with polycaprolactone.

95 weight parts of the surface-modified potassium oxide particles prepared in the foregoing manner were mixed with 5 weight parts of polyglycolide, and a bio-sponge was manufactured. Tensile strength, pH change, inflammation reaction, and cytotoxicity were then observed. As noted in Table 1, the results were similar to those of Example 1.

Example 6

40 weight parts of magnesium oxide, 42 weight parts of lactide and 18 weight parts of caprolactone were subjected to a ring-opening polymerization in the same manner as described in Example 1, to obtain magnesium oxide particles of which surface were modified with poly(lactide-co-caprolactone).

35 weight parts of the surface-modified magnesium oxide particles prepared in the foregoing manner were mixed with 65 weight parts of poly(lactide-co-caprolactone), and a hydrogel was manufactured. Tensile strength, pH change, inflammation reaction, and cytotoxicity were then observed. As noted in Table 1, the results were similar to those of Example 1.

Example 7

10 weight parts of sodium oxide and 90 weight parts of hydroxycaproic acid were subjected to a condensation polymerization in the same manner as described in Example 2, to obtain sodium oxide particles of which surface were modified with polycaprolactone.

10 weight parts of the surface-modified sodium oxide particles prepared in the foregoing manner were mixed with 90 weight parts of polypeptide, and a material for a neurological surgery was manufactured. Tensile strength, pH change, inflammation reaction, and cytotoxicity were then observed. As noted in Table 1, the results were similar to those of Example 1.

Example 8

50 weight parts of magnesium hydroxide, 25 weight parts of glycolic acid and 25 weight parts of hydroxycaproic acid were subjected to a condensation polymerization in the same manner as described in Example 2, to obtain magnesium hydroxide particles of which surface were modified with poly(glycolide-co-caprolactone).

5 weight parts of the surface-modified magnesium hydroxide particles prepared in the foregoing manner were mixed with 95 weight parts of polydioxanone, and a material for an orthopaedic surgery was manufactured. Tensile strength, pH change, inflammation reaction, and cytotoxicity were then observed. As noted in Table 1, the results were similar to those of Example 1.

Example 9

70 weight parts of magnesium oxide and 30 weight parts of polylactide were used to prepare magnesium oxide particles of which surface were modified with polylactide according to the core-shell method as described in Example 3.

70 weight parts of the surface-modified magnesium oxide particles prepared in the foregoing manner were mixed with 30 weight parts of polyhydroxy alkanoate, and a material for a plastic surgery was manufactured. Tensile strength, pH change, inflammation reaction, and cytotoxicity were then observed. As noted in Table 1, the results were similar to those of Example 1.

Example 10

20 weight parts of cesium oxide and 80 weight parts of polymaleic acid were used to prepare cesium oxide particles of which surface were modified with polymaleic acid according to the core-shell method as described in Example 3.

10 weight parts of the surface-modified cesium oxide particles prepared in the foregoing manner were mixed with 90 weight parts of polymaleic acid, and the resultant was coated on a cobalt-chromium stent. Tensile strength, pH change, inflammation reaction, and cytotoxicity were then observed. As noted in Table 1, the results were similar to those of Example 1.

Example 11

70 weight parts of calcium oxide and 30 weight parts of lactide were subjected to a ring-opening polymerization in the same manner as described in Example 1, to obtain calcium oxide particles of which surface were modified with polylactide.

40 weight parts of the surface-modified calcium oxide particles prepared in the foregoing manner were mixed with 60 weight parts of polylactide, and the resultant was coated on a titanium dental implant. Tensile strength, pH change, inflammation reaction, and cytotoxicity were then observed. As noted in Table 1, the results were similar to those of Example 1.

Example 12

40 weight parts of potassium hydroxide and 60 weight parts of trimethylenecarbonate were subjected to a ring-opening polymerization in the same manner as described in Example 1, to obtain potassium hydroxide particles of which surface were modified with polytrimethylenecarbonate.

20 weight parts of the surface-modified potassium hydroxide particles prepared in the foregoing manner were mixed with 80 weight parts of polyglycolide, and the resultant was coated on a hydroxyapatite material for an orthopaedic surgery. Tensile strength, pH change, inflammation reaction, and cytotoxicity were then observed. As noted in Table 1, the results were similar to those of Example 1.

Example 13

80 weight parts of magnesium oxide and 20 weight parts of hydroxycaproic acid were subjected to a condensation polymerization in the same manner as described in Example 2, to obtain magnesium oxide particles of which surface were modified with polycaprolactone.

50 weight parts of the surface-modified magnesium oxide particles prepared in the foregoing manner were mixed with 50 weight parts of polycaprolactone, and the resultant was coated on a surface of non-degradable polyurethane stent. Tensile strength, pH change, inflammation reaction, and cytotoxicity were then observed. As noted in Table 1, the results were similar to those of Example 1.

Comparative Example 1

A test sample was prepared using a polylactide biodegradable polymer which does not contain metal particles. Tensile strength, pH change, inflammation reaction, and cytotoxicity were then observed. As noted in Table 1, the tensile strength was relatively low, pH remained acidic, inflammation reactions were severe, and cytotoxicity was remarkable.

Comparative Example 2

5 weight parts of magnesium hydroxide particles of which surface were not modified were mixed with 95 weight parts of polylactide biodegradable polymer, and a sample was prepared a test sample with the resulting mixture. Tensile strength, pH change, inflammation reaction, and cytotoxicity were then observed. As noted in Table 1, the tensile strength was very low, pH remained slightly acidic, and inflammation reactions and the cytotoxicity were suppressed to some extent.

TABLE 1

Comparison of the characteristics of matrixes containing metal particles

| Example No. | Neutralizing metal particles | Tensile strength (Mpa) | pH (8 weeks) | Inflammation reaction | Cytotoxicity |
|---|---|---|---|---|---|
| Example 1 | Surface-modified | 56 | 7.2 | Completely suppressed | X |
| Example 2 | Surface-modified | 57 | 6.8 | Completely suppressed | X |
| Example 3 | Surface-modified | 55 | 7.1 | Completely suppressed | X |

TABLE 1-continued

Comparison of the characteristics of matrixes containing metal particles

| Example No. | Neutralizing metal particles | Tensile strength (Mpa) | pH (8 weeks) | Inflammation reaction | Cytotoxicity |
|---|---|---|---|---|---|
| Example 4 | Surface-modified | 57 | 6.9 | Completely suppressed | X |
| Example 5 | Surface-modified | 55 | 7.4 | Completely suppressed | X |
| Example 6 | Surface-modified | 54 | 7.1 | Completely suppressed | X |
| Example 7 | Surface-modified | 59 | 6.4 | Suppressed | Δ |
| Example 8 | Surface-modified | 61 | 6.1 | Suppressed | Δ |
| Example 9 | Surface-modified | 57 | 7.3 | Completely suppressed | X |
| Example 10 | Surface-modified | 53 | 6.3 | Suppressed | Δ |
| Example 11 | Surface-modified | 57 | 6.4 | Suppressed | |
| Example 12 | Surface-modified | 55 | 6.9 | Completely suppressed | X |
| Example 13 | Surface-modified | 53 | 6.7 | Completely suppressed | X |
| Comparative Example 1 | Not contained | 35 | 4.0 | Very severe | 0 |
| Comparative Example 2 | Surface-not modified | 26 | 5.8 | Suppressed | Δ |

(X: Survival of cells less than 10%, Δ: Survival of 10% to 30% of cells, 0: Survival of 30% or more of cells)

What is claimed is:

1. A biomedical implant consists of:
   surface-modified basic metal particles and a biodegradable polymer,
   wherein the surface-modified basic metal particles are basic metal particles whose surfaces are modified with a polymer;
   the basic metal particles suppress inflammation reactions caused by acidic byproducts generated from the degradation of the polymer, through neutralization reactions of the acidic byproducts and the basic metal particles; and
   the basic metal particles are any one selected from the group consisting of sodium hydroxide, magnesium hydroxide ($Mg(OH)_2$), calcium hydroxide ($Ca(OH)_2$) potassium hydroxide (KOH), barium hydroxide ($Ba(OH)_2$), and
   wherein a content of the surface-modified basic metal particles is 20 to 30 wt %, and a content of the biodegradable polymer is 70 to 80 wt %.

2. The biomedical implant according to claim 1, wherein the diameter of the basic metal particles ranges from 1 nm to 1 mm.

3. The biomedical implant according to claim 1, wherein the surface-modified basic metal particles are modified with the polymer which is generated by the polymerization of one or more monomers selected from the group consisting of lactide, glycolide, caprolactone, dioxanone, trimethylenecarbonate, hydroxyalkanoate, peptide, cyanoacrylate, lactic acid, glycolic acid, hydroxycaproic acid, maleic acid, phosphazene, amino acid, hydroxybutyric acid, sebacic acid, hydroxyethoxyacetic acid and trimethyleneglycol; or with a polymer selected from the group consisting of polylactide, polyglycolide, polycaprolactone, poly(lactide-co-glycolide), poly(lactide-co-caprolactone), poly(glycolide-co-caprolactone), polydioxanone, polytrimethylenecarbonate, poly(glycolide-co-dioxanone), polyamideester, polypeptide, polyorthoesters, polymaleic acid, polyphosphazene, polyanhydride, polycebacicanhydride, polyhydroxyalkanoate, polyhydroxybutyrate, and polycyanoacrylate.

4. The biomedical implant according to claim 1, wherein the biodegradable polymer is at least one selected from the group consisting of polylactide, polyglycolide, polycaprolactone, poly(lactide-co-glycolide), poly(lactide-co-caprolactone), poly(glycolide-co-caprolactone), polydioxanone, polytrimethylenecarbonate, poly(glycolide-co-dioxanone), polyamideester, polypeptide, polyorthoesters, polymaleic acid, polyphosphazene, polyanhydride, polycebacicanhydride, polyhydroxyalkanoate, polyhydroxybutylate, and polycyanoacrylate.

5. The biomedical implant according to claim 1, wherein the biomedical implant is selected from the group consisting of a cardiovascular system material selected from stent, suture for surgical operation, support for tissue regeneration, bio-nanofiber, hydrogel and bio-sponge; dental material selected from pin, screw and bar; and material for neurological, orthopaedic and plastic surgeries.

* * * * *